US007939081B2

(12) United States Patent
Hosoya et al.

(10) Patent No.: US 7,939,081 B2
(45) Date of Patent: May 10, 2011

(54) METHOD FOR PRODUCING CERCOSPORAMIDE

(75) Inventors: Tsuyoshi Hosoya, Ibaraki (JP); Jun Ohsumi, Kanagawa (JP); Kiyoshi Hamano, Kanagawa (JP); Yasunori Ono, Tokyo (JP); Masami Miura, Chiba (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 540 days.

(21) Appl. No.: 11/997,112

(22) PCT Filed: Aug. 8, 2006

(86) PCT No.: PCT/JP2006/315622

§ 371 (c)(1), (2), (4) Date: Apr. 7, 2008

(87) PCT Pub. No.: WO2007/018194
PCT Pub. Date: Feb. 15, 2007

(65) Prior Publication Data

US 2010/0152467 A1 Jun. 17, 2010

(30) Foreign Application Priority Data

Aug. 9, 2005 (JP) ................................ 2005-230624

(51) Int. Cl.

| | |
|---|---|
| *A61K 36/84* | (2006.01) |
| *C12P 21/04* | (2006.01) |
| *A01N 63/04* | (2006.01) |

(52) U.S. Cl. .................. 424/195.15; 435/71.3; 424/93.5

(58) Field of Classification Search ........................ None
See application file for complete search history.

(56) References Cited

U.S. PATENT DOCUMENTS

| | | | | |
|---|---|---|---|---|
| 4,983,587 | A | 1/1991 | Speakman | |
| 5,907,047 | A * | 5/1999 | Hanske et al. | 506/7 |
| 6,399,060 | B1 * | 6/2002 | Hiromoto | 424/115 |
| 2009/0036492 | A1 * | 2/2009 | Furukawa et al. | 514/337 |

OTHER PUBLICATIONS

Conover, M.A., et al., "Usnic Acid Amide, a Phytotoxin and Antifungal Agent From Cercosporidium henningsii," Phytochemistry 31(9):2999-3001, Jan. 1992.

European Search Report mailed Aug. 27, 2010, issued in corresponding European Application No. 06782463.1, filed Aug. 8, 2006, 7 pages.

International Preliminary Report on Patentability issued Feb. 12, 2008, in corresponding International Application No. PCT/JP2006/315622, filed Aug. 8, 2006, 6 pages.

International Search Report mailed Aug. 29, 2006, issued in corresponding International Application No. PCT/JP2006/315622, filed Aug. 8, 2006, 2 pages.

Cooper, A.B., et al., "Synthesis of (+)-8-Methyl Cercosporamide: Stereochemical Correlation of Natural (-)-Cercosporamide with (+)-Usnic Acid," Tetrahedron 48(23):4757-4766, 1992.

Hong, Z., et al., "Cloning and Characterization of KNR4, a Yeast Gene Involved in (1,3)-β-Glucan Synthesis," Molecular and Cellular Biology 14(2):1017-1025, Feb. 1994.

Stadler, M., et al., "Metabolites With Nematicidal and Antimicrobial Activities From the Ascomycete *Lachnum papyraceum* (Karst.) Karst: V. Production, Isolation and Biological Activities of Bromine-containing Mycorrhizin and Lachnumon Derivatives and Four Additional New Bioactive Metabolites," The Journal of Antibiotics 48(2):149-153, Feb. 1995.

Sugawara, F., et al., "The Structure and Biological Activity of Cercosporamide from *Cercosporidium henningsii*," Journal of Organic Chemistry 56:909-910, 1991.

* cited by examiner

*Primary Examiner* — Christopher R. Tate
(74) *Attorney, Agent, or Firm* — Christensen O'Connor Johnson Kindness PLLC

(57) ABSTRACT

The present invention provides a process for producing cercosporamide comprising culturing a fungus belonging to the genus *Lachnum* and/or fungus belonging to the genus *Pseudaegerita* and recovering cercosporamide from the culture thereof. In addition, the present invention provides cercosporamide acquired according to this production process. Further, the present invention provides novel microorganisms consisting of *Lachnum fuscescens* SANK 19096, *Lachnum calycioides* SANK 12497, *Lachnum caesaliatum* SANK 10906, and *Pseudaegerita websteri* SANK 11006.

4 Claims, 1 Drawing Sheet

METHOD FOR PRODUCING CERCOSPORAMIDE

TECHNICAL FIELD

The present invention relates to a process for producing cercosporamide using a fungus belonging to the genus *Lachnum* and/or belonging to the genus *Pseudaegerita*, cercosporamide produced according to said production process, and a fungus and the like that produces cercosporamide.

BACKGROUND ART

Cercosporamide is a natural substance isolated from cultures of the fungus *Cercosporidium heningsii* (see U.S. Pat. No. 4,983,587, The Journal of Organic Chemistry, 1991, Vol. 56, pp. 909-910, Tetrahedron, 1992, Vol. 48, pp. 4757-4766, and Molecular and Cellular Biology, 1994, Vol. 14, pp. 1017-1025).

Cercosporamide is known to have antifungal activity. In addition, some derivatives of cercosporamide are also known to have antifungal activity similar to that of cercosporamide (U.S. Pat. No. 4,983,587).

Cercosporamide is also useful as a precursor for synthesizing derivatives thereof, and there is currently a need for a more efficient production process.

Although the fungus *Cercosporidium heningsii* is known to be a microorganism that produces cercosporamide, fungi belonging to the genus *Lachnum* and *Pseudaegerita* were not known to produce cercosporamide.

DISCLOSURE OF THE INVENTION

Problems to be Solved by the Invention

An object of the present invention is to provide a cercosporamide production process using microorganisms. Another object of the present invention is to provide cercosporamide produced according to that production process. Still another object of the present invention is to provide a microorganism that produces cercosporamide.

As a result of conducting extensive studies to solve the aforementioned problems, the inventors of the present invention found that cercosporamide is produced by fungi belonging to the genera *Lachnum* and *Pseudaegerita*, and also discovered a process for producing cercosporamide by using those fungi, thereby leading to completion of the present invention.

Means for Solving the Problems

The present invention is composed of the following:

(1) a process for producing cercosporamide comprising: culturing a fungus belonging to the genus *Lachnum* and yielding cercosporamide from the culture thereof, (2) the process for producing cercosporamide described in (1) above, wherein the fungus belonging to the genus *Lachnum* is at least one fungus selected from the group consisting of *Lachnum fuscescens, Lachnum calycioides* and *Lachnum caesaliatum,*

(3) the process for producing cercosporamide described in (1) above, wherein the fungus belonging to the genus *Lachnum* is at least one fungus selected from the group consisting of *Lachnum fuscescens* SANK 19096, *Lachnum calycioides* SANK 12497 and *Lachnum caesaliatum* SANK 10906, (4) a process for producing cercosporamide comprising: culturing a fungus belonging to the genus *Pseudaegerita*, and yielding cercosporamide from the culture thereof, (5) the process for producing cercosporamide described in (4) above, wherein the fungus belonging to the genus *Pseudaegerita* is *Pseudaegerita websteri,*

(6) the process for producing cercosporamide described in (4) above, wherein the fungus belonging to the genus *Pseudaegerita* is *Pseudaegerita websteri* SANK 11006, (7) cercosporamide produced according to the production process described in any one of (1) to (6) above, (8) a pharmaceutical containing as an active ingredient thereof cercosporamide produced according to the production process described in any one of (1) to (6) above, (9) *Lachnum fuscescens* SANK 19096,

(10) *Lachnum calycioides* SANK 12497,

(11) *Lachnum caesaliatum* SANK 10906, and,

(12) *Pseudaegerita websteri* SANK 11006.

In the present specification, "cercosporamide" refers to the compound represented by the following formula (1).

(I)

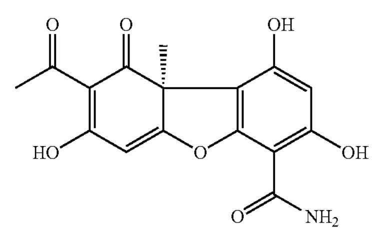

Cercosporamide exhibits the physicochemical properties indicated below.

1) Appearance: Weakly acidic, liposoluble, yellowish-brown powder

2) Molecular formula: $C_{16}H_3NO_7$

3) Molecular weight: 331 (as determined by EI mass spectrometry)

4) The exact mass as observed by high-resolution EI mass spectrometry $[M]^+$ (as $C_{16}H_{13}NO_7$) is as indicated below.
Found: 331.0690
Calculated: 331.0692

5) Specific rotatory power: $[\alpha]_D^{25}$ −396.4° (c 0.51, acetonitrile)

6) Proton-Nuclear magnetic resonance spectrum: (δ, ppm)

The $^{1}H$-nuclear magnetic resonance spectrum (500 MHz) as measured in deuterated heavy chloroform using the residual proton signal (7.27 ppm) as an internal standard is as indicated below.

1.75 (3H, s), 2.68 (3H, s), 5.99 (1H, s), 6.26 (1H, s), 6.38 (1H, s), 6.96 (1H, s), 10.55 (1H, s), 12.98 (1H, s), 18.83 (1H, s)

7) Carbon-13-Nuclear magnetic resonance spectrum: (δ, ppm)

The $^{13}C$-nuclear magnetic resonance spectrum (125 MHz) as measured in deuterated chloroform using the deuterated chloroform signal (77.23 ppm) as an internal standard is as indicated below.

27.9 (q), 32.1 (q), 58.8 (s), 94.0 (s), 99.4 (d), 101.5 (d), 104.0 (s), 105.6 (s), 155.2 (s), 158.1 (s), 166.1 (s), 169.8 (s), 178.2 (s), 191.8 (s), 197.7 (s), 201.9 (s)

Effects of the Invention

According to the present invention, a process for producing cercosporamide, cercosporamide produced according to said production process, and a fungus belonging to the genus *Lachnum* or the genus *Pseudaegerita* that produces cercosporamide are provided. Specific examples of fungi provided by the present invention that produce cercosporamide include *Lachnum fuscescens* SANK 19096, *Lachnum calycioides* SANK 12497, *Lachnum caesaliatum* SANK 10906 and *Pseudaegerita websteri* SANK 11006. In addition to cercosporamide itself being useful as an antifungal agent, it is also useful as a precursor for producing derivatives of cercosporamide.

BEST MODE FOR CARRYING OUT THE INVENTION

1. Cercosporamide-Producing Fungi

As a result of conducting an extensive search for microorganisms that produce cercosporamide, the inventors of the present invention found cercosporamide in the cultures of *Lachnum fuscescens* SANK 19096, *Lachnum calycioides* SANK 12497, *Lachnum caesaliatum* SANK 10906 and *Pseudaegerita websteri* SANK 11006.

The fungus that produces cercosporamide is not particularly limited so long as it belongs to the genus *Lachnum* and *Pseudaegerita*, it is preferably at least one fungus selected from the group consisting of *Lachnum fuscescens*, *Lachnum calycioides*, *Lachnum caesaliatum* and *Pseudaegerita websteri*, and more preferably at least one fungus selected from the group consisting of *Lachnum fuscescens* SANK 19096 (hereinafter referred to as "strain SANK 19096"), *Lachnum calycioides* SANK 12497 (hereinafter referred to as "strain SANK 12497"), *Lachnum caesaliatum* SANK 10906 (hereinafter referred to as "strain SANK 10906") and *Pseudaegerita websteri* SANK 11006 (hereinafter referred to as "strain SANK 11006").

The following indicates the mycological properties of strain SANK 19096, strain SANK 12497, strain SANK 10906 and strain SANK 11006.

In describing mycological characteristics, indication of colony coloring was in accordance with "Kornerup, A. and Wanscher, J. H. (1978), Methuen Handbook of Colour, 3rd ed., Eyre Methuen, London, UK, 1-252".

Observation of mycological properties during culturing of each fungus used the media indicated below.

Potato dextrose agar medium (hereinafter referred to as "PDA medium"): 39 g of Nissui Potato Dextrose Agar Medium (Nissui Pharmaceutical Co., Ltd.) is dissolved in 1000 ml of distilled water followed by sterilizing for 15 minutes at 121° C. and preparing plates.

Modified Weitzman and Silva-Hutner medium (hereinafter referred to as "WSH medium"): 10 g of Nisshoku Oatmeal, 1 g of magnesium sulfate heptahydrate, 1 g of potassium dihydrogenphosphate, 1 g of sodium nitrate and 20 g of agar are dissolved in 1000 ml of distilled water followed by sterilizing for 15 minutes at 121° C. and preparing plates.

Malt extract agar medium (hereinafter referred to as "MEA medium"): 20 g of malt extract, 1 g of polypepton (Nihon Pharmaceutical Co., Ltd.), 20 g of glucose and 20 g of agar are dissolved in 1000 ml of distilled water followed by sterilizing for 15 minutes at 121° C. and preparing plates.

Corn meal agar medium (hereinafter referred to as "CMA medium"): 17 g of Nissui Corn Meal Agar (Nissui Pharmaceutical Co., Ltd.) is dissolved in 1000 ml of distilled water followed by sterilizing for 15 minutes at 121° C. and preparing plates.

Abdullah's malt extract agar medium (hereinafter referred to as "AMEA medium"): 0.76 g of malt extract, 0.14 g of glycerol, 0.16 g of dextrin, 0.046 g of GE90M (DMV Co., Ltd.) and 15 g of agar are dissolved in 1000 ml of distilled water followed by sterilizing for 15 minutes at 121° C. and preparing plates.

PDA medium, WSH medium, CMA medium and MEA medium were used for strain SANK 19096, strain SANK 12497 and strain SANK 10906, while PDA medium, WSH medium, CMA medium and AMEA medium were used for strain SANK 11006.

(1) *Lachnum fuscescens* SANK 19096

*Lachnum fuscescens* SANK 19096 was isolated as *Lachnum* sp. SANK 19096 from fruiting bodies formed on fallen leaf collected in Nagano Prefecture, Japan.

The mycological properties of a dried fruiting body specimen used to isolate strain SANK 19096 are described as follows. Apothecium is short stipe; the disc is slightly concaved, 557 μm in diameter and pale brown when rehydrated with distilled water. The disc is deep cupulate with incurving margin, 499 μm in diameter and pale brown when dry. The ectal excipulum is "textura prismatica", hyaline to subhyaline, composed of thick-walled cells and with short hair-like projections or hairs from the outermost layer. The medullary excipulum is "textura intricata" and hyaline. The hairs are cylindrical, straight or slightly curved, obtuse at the apex, multi-septate, granulate all over, brown, 4.5 to 6.0 μm in width and 71 to 76 μm in length. Amorphous resinous matters are rarely attached to the ends of the hairs. The stipe is cylindrical, pale brown and 115 μm in height. The asci are inoperculate, cylindrical-clavate, 8-spored, 30 to 43 μm in length and 3.5 to 5 μm in width. The tip of the ascus is stained blue by Melzer's reagent. The paraphyses are lanceolate, aseptate or occasionally 1- or 2-septate, hyaline, 50.9 to 68.7 μm in length, 2.7 to 4.1 μm at the widest point and exceed the asci by 9.1 to 16.5 μm. The ascospores are fusiform to oblong-ellipsoid, aseptate, hyaline, 5.5 to 8.5 in length and 1.3 to 2.2 μm in width.

Strain SANK 19096 demonstrates the mycological properties indicated below on the various media described above.

Colonies on PDA medium reach a diameter of 19 to 21 mm following culturing for 21 days at 23° C. The colonies are velvety to cottony, composed of a mycelia layer protruding toward the center and reddish gray (11B2) to white. Exudates, sclerotia and conidia are not observed. The back of the colonies is grayish orange (5B4) in the center and white along the margins, have radiating wrinkles. Soluble pigment is not observed. Mycelia are septate, branched, hyaline and 1.5 to 3.5 μm in diameter.

Colonies on WSH medium reach a diameter of 29 to 31 mm following culturing for 21 days at 23° C. The colonies are floccose to velvety, composed of a thin mycelia layer and white. Exudates, sclerotia and conidia are not observed. The back of the colonies is white. Soluble pigments are not observed.

Colonies on CMA medium reach a diameter of 33 to 34 mm following culturing for 21 days at 23° C. The colonies consist only of an extremely thin mycelia layer and are colorless. Exudates, sclerotia and conidia are not observed. The back of the colonies is colorless. Soluble pigments are not observed.

Colonies on MEA medium reach a diameter of 21 to 22 mm following culturing for 21 days at 23° C. The colonies are cottony in the center, mycelia concentrate toward the margins and become velvety and grayish yellow (4C4) to yellowish white (4A1), while the concentrated portion of airborne mycelia are white. The margins are composed only of basal mycelia and brownish orange (5C3) to orange gray (5C2). Exudates, sclerotia and conidia are not observed. The back of the colonies is yellowish brown (5D6) to grayish orange (5B3) and white along the margins. Soluble pigments are not observed.

The morphological characteristics of the present fungus agreed well with the description of *Lachnum* species in the document by Spooner (Spooner, B M (1987) Bibliotheca Mycologica 116: 1-711). Thus, this fungus was identified as *Lachnum* sp. and named *Lachnum* sp. strain SANK 19096.

Strain SANK 19096 agreed, with only few exceptions, with the descriptions of *Dasyscyphus fuscescens* (Pers.) Gray of the document by Dennis, R W G (Dennis, R W G (1949) Mycological Papers 32: 1-97) and *Lachnum fuscescens* (Pers.) P. Karst. in the document by Tanaka and Hosoya (Tanaka, I and Hosoya, T (2001) Mycoscience 42: 597-609). *Dasyscyphus fuscescens* is currently treated as a synonym of *Lachnum fuscescens*. In addition, in a document by Baral and Krieglsteiner (Baral, H O and Krieglsteiner, G J (1985) Beihefte zur Zeitschrift für Mykologie 6: 1-160), a new genus *Brunnipila* is established for *Lachnum* species having brown hairs in the manner of *Lachnum fuscescens*, and is treated as a different genus. In the document by Baral and Krieglsteiner, *Lachnum fuscescens* is treated as a synonym of *Brunnipila fuscescens* (Pers.) Baral. However, this approach is not widely accepted, and in the publication by Krik, et al. (Krik, P M et al. (2001) Ainsworth & Bisby's Dictionary of Fungi 9th Edition, CABI International, Wallingford, UK, 1-655), the genus *Brunnipila* is treated as a synonym of the genus *Lachnum*. Thus, in the present patent, strain SANK 19096 was identified as *Lachnum fuscescens* in accordance with the document by Tanaka and Hosoya, and was named *Lachnum fuscescens* SANK 19096.

Strain SANK 19096 was internationally deposited as *Lachnum* sp. SANK 19096 on May 24, 2005 at the International Patent Organism Depository of the National Institute of Advanced Industrial Science and Technology (location: Chuo #6, 1-1-1 Higashi, Tsukuba City, Ibaraki Prefecture, Japan), and was assigned the deposit number FERM BP-10338.

(2) *Lachnum calycioides* SANK 12497

The mycological properties of strain SANK 12497 are indicated below.

*Lachnum calycioides* SANK 12497 was isolated from fruiting bodies formed on the dried stems of grass collected in Tottori Prefecture, Japan.

The mycological properties of dried fruiting body specimens used to isolate strain SANK 12497 are described as follows. Apothecia are scattered or clustered, stipitate, the margins curve to the inside when dry, 1271 to 1817 μm in height and 437 to 913 μm in diameter; the surface are grayish orange (6B4); the hairs are light brown (7D4) to dark brown (7F7); the stipes and ectal excipulum are grayish orange (6B4). The ectal excipulum is "textura prismatica", hyaline to brown in color, composed of thick-walled cells and with short hair-like projections or hairs from the outermost layer. The medullary excipulum is "textura intricata" and hyaline. The hairs are cylindrical, straight or somewhat curved, obtuse at the apex, multi-septate, granulate all over, brown, 3.8 to 5.5 μm in width and 58.1 to 111.6 μm in length. Amorphous matters are attached to the ends of the hairs, and ascospores are frequently attached thereon. The stipes are cylindrical, 908 to 1374 μm in length, 170 to 205 μm in diameter and hyaline to brown. The asci are inoperculate, cylindrical-clavate, conical apex, 8-spored, 69.3 to 80.2 μm in length and 3.9 to 6.8 μm in width. The tip of the ascus is stained blue by Melzer's reagent following treatment with 3% KOH. The paraphyses are lanceolate, aseptate or occasionally 1- or 3-septate, hyaline, 98.1 to 130.2 in length, 4.4 to 7.0 μm at the widest point and exceed the asci by 13.5 to 36.0 μm. The ascospores are fusiform to oblong-ellipsoid, aseptate, hyaline, 8.8 to 15.6 μm in length and 1.8 to 3.0 μm in width.

Strain SANK 12497 demonstrates the mycological properties indicated below on the various media described above.

Colonies on PDA medium reach a diameter of 21 to 25 mm following culturing for 21 days at 23° C. The colonies are velvety to cottony, composed of a mycelia layer somewhat protruding toward the center and reddish brown (8E2) to grayish orange (5B3). The margins of the colonies are irregularly laciniated. Exudates, sclerotia and conidia are not observed. The back of the colonies is dark brown (6F4) to grayish orange (5B3) in the center and white along the margins, having radiating wrinkles. Soluble pigment is not produced. Mycelia are septate, branched, hyaline to pale brown and 1.3 to 2.6 μm in diameter.

Colonies on WSH medium reach a diameter of 32 to 34 mm following culturing for 21 days at 23° C. The colonies are composed of a thin mycelia layer, light yellow (2A5) to white. The margins of the colonies are smooth. Exudates, sclerotia and conidia are not observed. The back of the colonies is the same as that of the surface. Soluble pigment is not produced.

Colonies on CMA medium reach a diameter of 33 to 35 mm following culturing for 21 days at 23° C. The colonies are composed only of an extremely thin mycelia layer and colorless. The margins of the colonies are smooth. Exudates, sclerotia and conidia are not observed. The back of the colonies has the same color as that of the surface. Soluble pigment is not produced.

Colonies on MEA medium reach a diameter of 18 to 27 mm following culturing for 21 days at 23° C. The colonies are thin and velvety, have wrinkles radiating toward the margins and are grayish orange (5B6) to light yellow (3A4). The margins of the colonies are rarely gently involuted. Exudates, sclerotia and conidia are not observed. The back of the colonies is grayish orange (5B6) to orange gray (5B2), and white along the margins. Soluble pigment is not produced.

The morphological characteristics of the present fungus agreed well with the description of *Lachnum* species in the document by Spooner (Spooner, B M (1987) Bibliotheca Mycologica 116: 1-711). Moreover, morphological characteristics also agreed, with only few exceptions, with the descriptions of *Lachnum calycioides* (Rehm) Rehm of the publication by Rehm (Rehm, H (1986) Dr. Rabenhorst's Kryptogamen-Flora von Deutschland, Oesterreichs und der Schweiz Zweite Auflage. Vol. 1. III. Abtheilung: Ascomyceten: Hysteriaceen und Discomyceten, Eduard Kummer, Leipzig, Germany, 1-1275), *Dasyscyphus calycioides* (Rehm) Sacc. of the publication by Brietenbach and Kranzlin (Brietenbach, J & Kranzlin, F (1984) Fungi of Switzerland. Vol. 1 Ascomycetes, Verlag Mykologia, Luzern Switzerland, 1-310), and *Brunnipila calycioides* (Rehm) Baral of the document by Scheuer (Scheuer, C (1988) Bibliotheca Mycologica 123: 1-274). *Lachnum calycioides*, *Dasyscyphus calycioides* and *Brunnipila calycioides* are synonyms of the same species. *Dasyscyphus calycioides* is considered to be a synonym of *Brunnipila calycioides* in the document by Baral and Krieglsteiner (Baral, H O and Krieglsteiner, G J (1985) Beihefte zur Zeitschrift für Mykologie 6: 1-160). However, the genus *Brunnipila* used in the document of Scheuer (1988) is not widely accepted, and the genus *Brunnipila* is treated as a synonym of the genus *Lachnum* in the publication by Krik, et al. (Krik, P M et al. (2001) Ainsworth & Bisby's Dictionary of Fungi 9th Edition, CABI International, Wallingford, UK, 1-655). Thus, in the present patent, strain SANK 12497 was identified as *Lachnum calycioides* and named *Lachnum calycioides* SANK 12497.

Strain SANK 12497 was internationally deposited as *Lachnum calycioides* SANK 12497 on Jun. 29, 2006 at the International Patent Organism Depository of the National Institute of Advanced Industrial Science and Technology (location: Chuo #6, 1-1-1 Higashi, Tsukuba City, Ibaraki Prefecture, Japan), and was assigned the deposit number FERM BP-10636.

(3) *Lachnum caesaliatum* SANK 10906

The mycological properties of strain SANK 10906 are indicated below.

*Lachnum caesaliatum* SANK 10906 was isolated from fruiting bodies formed on fallen leaves collected in Kanagawa Prefecture, Japan.

The mycological properties of dried fruiting body specimens used to isolate strain SANK 10906 are described as follows. Apothecia are scattered or clustered, stipitate, the margins curve to the inside when dry, dark orange (5A8), 391 to 858 μm in height and 212 to 446 μm in diameter; the hairs are white; the stipes and ectal excipulum are light orange (6A5). The discs are 532 to 739 μm, slightly concave and pale orange color overall when rehydrated with distilled water.

The ectal excipulum is "textura prismatica", hyaline to pale brown, composed of thick-walled cells and with short hair-like projections or hairs from the outermost layer. The medullary excipulum is "textura intricata" and hyaline. The hairs are cylindrical, straight or slightly curved, obtuse at the apex, multi-septate, granulate all over, hyaline, 2.1 to 2.7 μm in width and 43.9 to 98.9 μm in length. The stipes are cylindrical, hyaline to pale brown, 310 to 530 μm in length and 55 to 90 μm in diameter. The asci are inoperculate, cylindrical-clavate, 8-spored, 29.8 to 42.0 μm in length and 3.6 to 5.4 μm in width. The tip of the ascus is stained blue by Melzer's reagent following treatment with 3% KOH. The paraphyses are lanceolate, aseptate, hyaline, 33.9 to 42.6 μm in length, 1.4 to 2.8 μm at the widest point and exceed the asci by 5 to 9.5 μm. The ascospores are fusiform to oblong-ellipsoid, aseptate, hyaline, 11.4 to 17.2 μm in length and 1.5 to 2.4 μm in width.

Strain SANK 10906 demonstrates the mycological properties indicated below on the various media described above.

Colonies on PDA medium reach a diameter of 10 to 12 mm following culturing for 21 days at 23° C. The colonies are velvety to cottony and grayish yellow (4C7) to light yellow (4A5). The margins of the colonies are white and irregularly laciniated. Exudates, sclerotia and conidia are not observed. The back of the colonies is yellowish brown (5F8-5E6) in the center and white along the margins. Soluble pigment is not produced. Mycelia are septate, branched, light brown to hyaline and 1.7 to 5.1 μm in diameter.

Colonies on WSH medium reach a diameter of 17 to 20 mm following culturing for 21 days at 23° C. The colonies are composed of a thin mycelia layer, partially form white, cottony, airborne mycelia and are white. The margins of the colonies are smooth. Exudates, sclerotia and conidia are not observed. The back of the colonies is white. Soluble pigments are not produced.

Colonies on CMA medium reach a diameter of 30 to 34 mm following culturing for 21 days at 23° C. The colonies consist only of an extremely thin mycelia layer and are colorless. The margins of the colonies are smooth. Exudates, sclerotia and conidia are not observed. The back of the colonies is colorless. Soluble pigments are not produced.

Colonies on MEA medium reach a diameter of 8 to 11 mm following culturing for 21 days at 23° C. The colonies are velvety and brownish orange (5C4) to grayish orange (5B3). The margins of the colonies are white and rarely gently laciniated. Exudates, sclerotia and conidia are not observed. The back of the colonies is yellowish brown (5F8) to golden brown (5D8) and white along the margins. Soluble pigments are not produced.

The morphological characteristics of the present fungus agreed well with the description of *Lachnum* species in the document by Spooner (Spooner, B M (1987) Bibliotheca Mycologica 116: 1-711). Among existing *Lachnum* species, strain SANK 10906 resembles *Lachnum pteridophyllum* (Rodway) Spooner and *Lachnum varians* (Rehm) M. P. Sharma described in the document by Spooner. However, in contrast to strain SANK 10906 being isolated from fallen leaves of woody plants, *Lachnum pteridophyllum* and *Lachnum varians* are clearly distinguished from strain SANK 10906 since they previously have only been isolated from Cyatheaceae hosts and have longer asci and broader hairs than strain SANK 10906. Therefore, strain SANK 10906 was identified as a new species of the genus *Lachnum* and is tentatively named as *Lachnum caesaliatum*, and subsequently named *Lachnum caesaliatum* SANK 10906.

Strain SANK 10906 was internationally deposited as *Lachnum caesaliatum* SANK 10906 on Jun. 29, 2006 at the International Patent Organism Depository of the National Institute of Advanced Industrial Science and Technology (location: Chuo #6, 1-1-1 Higashi, Tsukuba City, Ibaraki Prefecture, Japan), and was assigned the deposit number FERM BP-10634.

(4) *Pseudaegerita websteri* SANK 11006

The mycological properties of strain SANK 11006 are indicated below.

*Pseudaegerita websteri* SANK 11006 was isolated from propagules formed on fallen branches collected in Miyazaki Prefecture, Japan.

The mycological properties of propagules on AMEA medium following culturing for 28 days at 15° C. and on dried specimens used for isolation of strain SANK 11006 are described below.

Mycelia on AMEA medium are superficial or immersed, septate, branched, brown to hyaline and 1.3 to 3.2 μm in diameter. Conidiophores are solitary, micronematous or semi-macronematous and septate. Conidiogenous cells are polyblastic. Propagules are globose to subglobose, scattered on the surface of the substrate, rarely aggregated, white and 26.6 to 80.9 μm in diameter. Propagules are composed of clusters of highly branched structures, and each cell is spherical to ellipsoidal and 3.6 to 5.6 μm in diameter. There are spaces between each cell, each successively budding out 1 to 4 daughter cells. *Phialidic conidia* are not observed. Propagules formed on fallen branches are nearly identical to those on AMEA medium, 37.0 to 106.0 μm in diameter, and each cell is 3.4 to 6.8 μm in diameter. *Phialidic conidia* are not observed.

Strain SANK 11006 demonstrates the mycological properties indicated below on the various media described above.

Colonies on PDA medium reach a diameter of 13 to 14 mm following culturing for 28 days at 15° C. The colonies are velvety, composed of a mycelia layer protruding toward the center and olive (2F6) to olive gray (2D2). The margins of the colonies are slightly laciniated. Exudates, sclerotia and propagules are not observed. The back of the colonies is the same color as the surface. Soluble pigment is not produced. Mycelia are septate, branched, reddish brown to hyaline and 1.6 to 3.0 μm in diameter.

Colonies on WSH medium reach a diameter of 13 mm following culturing for 28 days at 15° C. The colonies are composed of a thin mycelia layer and wooly airborne mycelia and are olive (2F4-2E5). The margins of the colonies are smooth. Exudates, sclerotia and propagules are not observed.

The back of the colonies exhibits olive (2F7) to olive gray (2F2). Soluble pigments are not produced.

Colonies on CMA medium reach a diameter of 13 to 18 mm following culturing for 28 days at 15° C. The colonies consist only of a thin mycelia layer and are olive (3F3) to grayish yellow (3B3). The margins of the colonies are smooth. White propagules are sparsely produced from the center to the margins of the colonies. Exudates and sclerotia are not observed. The back of the colonies is the same color as the surface. Soluble pigments are not produced.

Colonies on AMEA medium reach a diameter of 6 to 16 mm following culturing for 28 days at 15° C. The colonies are composed only of a thin mycelia layer and are olive (3F3) to grayish yellow (3B3). White propagules are sparsely produced from the center to the margins of the colonies. Exudates and sclerotia are not observed. The back of the colonies is the same color as the surface. Soluble pigments are not produced.

The morphological characteristics of the present fungus agreed, with only few exceptions, with the description of species of *Pseudaegerita websteri* Abdullah & Guarro of the document by Abdullah et al. (Abdullah, S K et al. (2005) Mycological Research 109: 590-594). There were only small differences between strain SANK 11006 and the descriptions of *Pseudaegerita websteri*, with the diameter of individual cells of the propagules being described as 3 to 4 μm for *Pseudaegerita websteri* and being described as 3.6 to 5.6 μm for strain SANK 11006. Thus, this fungus was identified as *Pseudaegerita websteri*, and named *Pseudaegerita websteri* SANK 11006.

Strain SANK 11006 was internationally deposited as *Pseudaegerita websteri* SANK 11006 on Jun. 29, 2006 at the International Patent Organism Depository of the National Institute of Advanced Industrial Science and Technology (location: Chuo #6, 1-1-1 Higashi, Tsukuba City, Ibaraki Prefecture, Japan), and was assigned the deposit number FERM BP-10635.

As is commonly known, fungi are susceptible to mutation either naturally or by artificial manipulation (such as by irradiating with ultraviolet light, irradiating with radiation or treating with chemicals or drugs), and this applies similarly to the strains SANK 19096, SANK 12497, SANK 10906 and SANK 11006 of the present invention. All mutant strains of these strains SANK 19096, SANK 12497, SANK 10906 and SANK 11006 are included in the present invention.

In addition, strains obtained by genetic techniques such as recombination, transduction or transformation are also included in these mutant strains. Namely, cercosporamide-producing strain SANK 19096, strain SANK 12497, strain SANK 10906, strain SANK 11006, mutant strains thereof and mycotic strains not clearly distinguished therefrom are all included in strains SANK 19096, SANK 12497, SANK 10906 and SANK 11006.

2. Fermentation

Cercosporamide producers can be cultured using media containing a carbon source, a nitrogen source and an inorganic salt capable of being assimilated by microorganisms in the manner of that ordinarily used for fermentative production by microorganisms.

Examples of carbon sources include glucose, fructose, maltose, sucrose, mannitol, glycerin, dextrin, oats, rye, pressed barley, cornstarch, potato, cornmeal, soybean meal, cottonseed oil, molasses, citric acid and tartaric acid, and these can be used alone or two or more can be used in combination. The content of the carbon source normally varies between 1 and 10% by weight of the amount of medium.

Examples of nitrogen sources that can be used include substances containing protein or hydrolysates thereof and inorganic salts. Specific examples of such nitrogen sources include soybean meal, wheat bran, peanut meal, cottonseed oil, casein hydrolysates, farmamine, fish meal, corn steep liquor, peptone, meat extract, yeast, yeast extract, malt extract, sodium nitrate, ammonium nitrate and ammonium sulfate, and these can be used alone or two or more can be used in combination. The content of the nitrogen source normally varies between 0.1 and 10% by weight of the amount of medium.

Examples of nutritive inorganic salts that can be used include ordinary salts and metal salts capable of providing ions. Specific examples of salts include sodium, ammonium, calcium, phosphate, sulfate, chloride and carbonate salts. Specific examples of metal salts include potassium, calcium, cobalt, manganese, iron and magnesium salts.

In addition, vitamins such as vitamin B1 or biotin, mycelium growth promoters such as thiamine and the like may also be added if necessary.

For liquid culturing of cercosporamide producers, silicone oil, vegetable oil or surfactant and the like can be used as an antifoaming agent. Although the pH of the medium when culturing any fungus selected from the group consisting of strain SANK 19096, strain SANK 12497, strain SANK 10906 and strain SANK 11006 for the purpose of production of cercosporamide varies according to the medium components, growth temperature and the like, a pH ordinarily used for the production of fermentation products may be adopted.

Although varying according to medium components, pH and the like, the temperature for the fermentation of strain SANK 19096, strain SANK 12497, strain SANK 10906 and strain SANK 11006 is normally 10 to 30° C., and a temperature range of 20 to 26° C. is favorable for growth. A fermentation temperature of 23 to 26° C. is preferred for the production of cercosporamide.

There are no particular limitations on the fermentation method for producing cercosporamide, and any method commonly used to culture microorganisms may be used. Examples of methods that can be used include solid culture, agitation culture, shaking culture and aeration-agitation culture.

Although the following indicates a fermentation method of culturing strain SANK 19096 as an example of a method for producing cercosporamide, the fermentation method is not limited to this method provided it is used to produce cercosporamide.

Fermentation of strain SANK 19096 normally starts with a seed culture comprised of one or two or more stages followed by shaking on a rotary shaker for 5 to 10 days (and preferably 7 days) at 20 to 26° C. (and preferably 26° C.) or until the seed culture grows sufficiently.

In the case of solid culturing of strain SANK 19096, the aforementioned seed culture broth can be inoculated into a final fermentation medium in a solid medium culture vessel such as an Erlenmeyer flask. Fermentation is carried out in the form of a standing culture by allowing the solid culture vessel to stand for 10 to 20 days (and preferably 14 days) at 20 to 26° C. (and preferably 26° C.). The desired cercosporamide can be obtained from final fermentation medium (cultured material).

In the case of liquid culturing of strain SANK 19096 on a comparatively small scale, the seed culture broth is inoculated into an Erlenmeyer flask containing the final fermentation medium followed by shaking on a rotary shaker at 20 to 26° C. (and preferably 26° C.) for several days. The desired cercosporamide can be obtained from the resulting fermented broth (culture).

On the other hand, in the case of liquid culturing of strain SANK 19096 on a comparatively large scale, it is preferred to use a suitable fermentation tank equipped with an agitator, an aeration apparatus, temperature controller and the like. The use of such an apparatus makes it possible to prepare the medium in advance in said tank. For example, the final production medium is heated at 121° C. for sterilization and then chilled. Next, the final production medium is inoculated with the seed culture followed by final fermentation while aerating and agitating at 26° C. The desired cercosporamide can be obtained from the resulting fermented broth (cultured material). This type of fermentation method allows the desired cercosporamide to be produced in large quantities.

In the case of producing cercosporamide by fermentation of a cercosporamide producer of the present invention, the amount of cercosporamide produced in said culture can be monitored at time intervals by high-performance liquid chromatography (HPLC) and the like to be described later. In the case of monitoring by HPLC analysis, the product is previously extracted from the culture with a hydrophilic solvent such as acetone followed by evaporation of said hydrophilic solvent and extracting with a solvent that is not miscible with water such as ethyl acetate. Next, after evaporation of the water-immiscible solvent, the product dissolved in a suitable solvent is preferably subjected to analysis or testing.

3. Extraction and Purification of Cercosporamide

Cercosporamide can be extracted from a fermented solid medium (cultured material) or a fermented liquid medium (cultured material) of a cercosporamide producer according to a method indicated in the previous section "2. Fermentation". There are no particular limitations on the methods used to extract and purify cercosporamide providing cercosporamide can be extracted and purified.

For example, after the completion of liquid fermentation of a cercosporamide producer, an organic solvent miscible with water such as acetone is added to the fermented broth (cultured material), the extract is separated into a soluble fraction (culture supernatant) and insoluble fraction (mycelium) by a filtration procedure using diatomaceous earth as an aid, or by a centrifugation procedure, and cercosporamide present in the resulting culture supernatant can be further extracted and purified by utilizing the physicochemical properties of the cercosporamide. In addition, as another method, after adding a filtration aid such as Celite to a fermented broth (cultured material) following completion of liquid fermentation of a cercosporamide producer, the fermented broth is filtered, the insoluble fraction containing the resulting mycelium is immersed in an aqueous solution of a solvent miscible with water such as acetone, and the cercosporamide can then be yielded by further extraction and purification from the mycelium extract by utilizing the physicochemical properties thereof.

Examples of methods for the purification of cercosporamide from culture supernatant include, but are not limited to, an extraction method by adding an acidic substance such as hydrochloric acid to the culture supernatant to adjust the pH to 3.0 followed by the addition of ethyl acetate.

The resulting extract can be purified by adsorption column chromatography using a carrier such as silica gel or magnesium-silica gel-based Florisil, thin layer chromatography, partition column chromatography using TSK Gel ToyoPearl HW-40F (registered trademark, Tosoh Corp.) or Sephadex LH-20 (registered trademark, Amersham Biosciences K.K.) and the like, reverse phase column chromatography using Cosmosil 140C18 (registered trademark, Nacalai Tesque Inc.), or HPLC using a normal phase or reversed phase column to isolate the desired cercosporamide.

The behavior of the compound in each purification step during purification of the cercosporamide of the present invention can be monitored, for example, by HPLC under the conditions indicated below.

(HPLC Conditions for Detecting Cercosporamide)

Separation column: YMC J'sphere ODS-H80 S-4, 4.6×150 mm (YMC Co., Ltd.)

Mobile phase: acetonitrile: 0.4% triethylamine-phosphate buffer (pH 3.2) (45:55)

Flow rate: 1.0 ml/minute

Detection: Ultraviolet absorption at, 225 nm

Retention time: 9.3 minute

4. Pharmaceutical Medicine Containing Cercosporamide

Cercosporamide of the present invention, or a salt thereof, can be in various forms when administered as a pharmaceutical medicine to a human or to an animal other than a human. The administration form thereof is dependent on the preparation, age, gender, disease and the like. For example, a tablet, pill, powder, granule, syrup, liquid, suspension, emulsion, granule, capsule or the like is administered orally. An injection preparation or the like is administered by intravenous administration, intramuscular administration, intracutaneous administration, subcutaneous administration or intraperitoneal administration. A suppository is administered rectally. An ointment or the like is used as an externally applied preparation.

A pharmaceutical preparation containing cercosporamide as an active ingredient thereof can be produced in accordance with ordinary methods using known auxiliaries normally able to be used in the field of pharmaceutical preparations, examples of which include excipients, binders, disintegrants, lubricants, dissolving agents, corrigents and coatings.

When forming into the form of a tablet, carriers known in the relevant field can be widely used for the carrier, examples of which include excipients such as lactose, saccharose, sodium chloride, glucose, urea, starch, calcium carbonate, kaolin, crystalline cellulose or silicic acid, binders such as water, ethanol, propanol, simple syrup, glucose solution, starch solution, gelatin solution, carboxymethyl cellulose, shellac, methyl cellulose, potassium phosphate or polyvinyl pyrrolidone, disintegrants such as dry starch, sodium alginate, powdered agar, powdered laminarin, sodium hydrogencarbonate, calcium carbonate, polyoxyethylene sorbitan fatty acid esters, sodium lauryl sulfate, monoglyceride stearate, starch or lactose, disintegration inhibitors such as saccharose, stearine, cocoa butter or hydrogenated oil, absorption promoters such as quaternary ammonium salts or sodium lauryl sulfate, moisture retention agents such as glycerin or starch, adsorbents such as starch, lactose, kaolin, bentonite or colloidal silicic acid, and lubricants such as purified talc, stearates, powdered boric acid or polyethylene glycol. Tablets can be provided with an ordinary coating as necessary, such as sugar-coated tablets, gelatin-coated tablets, enteric-coated tablets, film-coated tablets or double-layer or multilayer tablets.

When forming into the form of a pill, carriers known in the relevant field can be widely used for the carrier, examples of which include excipients such as glucose, lactose, starch, cocoa butter, hydrogenated oil, kaolin or talc, binders such as powdered gum Arabic, powdered tragacanth, gelatin or ethanol, and disintegrants such as laminarin or agar.

In the case of formulating as an injection preparation, it is preferable that a liquid or suspension be sterilized and be made isotonic with blood, and when forming into the form of a liquid, emulsion or suspension, diluents known in the relevant field can be widely used for the diluent, examples of which include water, ethyl alcohol, propylene glycol, epoxidated isostearyl alcohol, epoxidated stearyl alcohol, polyoxidated isostearyl alcohol and polyoxyethylene sorbitan fatty acid esters. An adequate amount of salt, glucose or glycerin may be contained to maintain isotonicity. Dissolving aids, buffers, indolent sugars, colorants, preservatives, fragrances, flavorings, sweeteners or other drugs and the like may also be contained.

Furthermore, in the case of intravenous administration of an injection preparation, the injection preparation is administered alone, after mixing with an ordinary supplement such as glucose or amino acid, or as an emulsion with a polyoxyethylene sorbitan fatty acid ester and the like.

When forming into the form of a suppository, carriers known in the relevant field can be widely used for the carrier, examples of which include polyethylene glycol, cocoa butter, higher alcohols, esters of higher alcohols, gelatin and semisynthetic glycerides.

When forming into the form of an externally applied preparation such as ointment, an excipient known in the relevant field belonging to any of a hydrophobic base (oily ointment base), hydroscopic base, hydrophilic base (cream) and water-soluble base (non-grease-based ointment) can be widely used for the excipient.

Although there are no particular limitations on the amount of cercosporamide or salt thereof contained in the aforementioned pharmaceutical preparations, the upper limit thereof is 30 to 70% by weight, the lower limit is 1% by weight, and the preferred range is 1 to 30% by weight.

Although dependent on symptoms, age, body weight, administration method, drug form and the like, the daily dosage of cercosporamide or a salt thereof for an adult has an upper limit of 100 to 1,000 mg, and a lower limit of 1 to 10 mg, and the preferred range is 10 to 100 mg.

The number of administrations of cercosporamide or salt thereof is once every several days, once a day or several times per day.

The present invention also provides a method for treating or preventing infections comprising the administration of a pharmaceutically effective amount of cercosporamide or a salt thereof, and the use of cercosporamide or a salt thereof for treating or preventing these diseases.

5. Synthesis of Cercosporamide Derivatives

Cercosporamide produced according to the production process of the present invention can be used as a precursor of derivatives thereof. Although known derivatives of cercosporamide include derivatives in which hydroxyl groups of cercosporamide are chemically modified with ether bonds, there are no particular limitations on these derivatives provided they are able to use cercosporamide as a precursor thereof.

EXAMPLES

The present invention is explained below by way of examples thereof, but the present invention is not limited thereto.

Example 1

Fermentation of *Lachnum fuscescens* SANK 19096 (FERM BP-10338) with Flask

A section of mycelia measuring about 5 mm on each side was cut out from a slant growing of strain SANK 19096 and was suspended in about 2 ml of physiological saline and homogenized with a glass potter. The entire amount was then aseptically inoculated into a 100 ml volumetric Erlenmeyer flask containing 30 ml of the medium shown in Table 1 (referred to as "Medium A"). Pre-culture was then carried out for 5 days at 23° C. and 210 revolutions per minute (abbreviated as "rpm") on a rotary shaker.

After the resulting pre-culture was inoculated at 5% (volume/volume) (abbreviated as "v/v") into a 500 ml volumetric Erlenmeyer flask containing 80 ml of Medium A, fermentation was carried out for 7 days at 26° C. and 210 rpm on a rotary shaker. HPLC analysis was then carried out under the conditions to be described later. At that time, a peak which possessed an equal retention time of cercosporamide (FIG. 1) was observed in the culture, thereby enabling confirmation of the production of cercosporamide by strain SANK 19096. The peak at 9.315 minutes in FIG. 1 indicates cercosporamide.

TABLE 1

| Medium A: Medium Composition | |
|---|---|
| Sucrose | 20 g |
| Raw potato | 100 g |
| Polypepton | 10 g |
| Potassium dihydrogenphosphate | 5 g |
| Magnesium sulfate heptahydrate | 2.5 g |
| Antifoaming agent CB-442 (NOF Corp.) | 100 mg |
| Tap water | 1000 ml |

The medium was sterilized at 121° C. for 20 minutes without adjusting pH.

HPLC analysis was carried out under the conditions indicated below.

Separation column: YMC J'sphere ODS-H80 S-4, 4.60×150 mm (YMC Co., Ltd.)
Mobile phase: acetonitrile: 0.4% triethylamine-phosphate buffer (pH 3.2) (45:55)
Flow rate: 1.0 ml/minute
Detection: Ultraviolet absorption at 225 nm
Retention time: 9.3 minutes

Example 2

Large-Scale Fermentation of *Lachnum fuscescens* SANK 19096 (FERM BP-10338)

A section of mycelia from a slant growing of strain SANK 19096 was suspended in about 2 ml of physiological saline and homogenized with a glass potter. The entire amount was inoculated into a 100 ml volumetric Erlenmeyer flask containing 30 ml of the medium shown in Table 2 (referred to as "Medium B") followed by cultivation for 7 days at 23° C. and 210 rpm on a rotary shaker. Following completion of the culture, an equal volume of 20% glycerol was added and mixed into the culture broth. This mixture was then stored at −80° C. and used as a seed culture broth for further use.

2 ml of the seed culture broth was inoculated into a 100 ml volumetric Erlenmeyer flask containing 30 ml of Medium B.

The initial pre-cultivation (first pre-cultivation) was carried out for 5 days at 23° C. and 210 rpm on a rotary shaker.

Culture broth obtained in the first pre-culture (first pre-culture broth) was inoculated at 5% (v/v) into a 2 L volumetric Erlenmeyer flask containing 500 ml of Medium B followed by carrying out a second process of pre-culture (second pre-cultivation) for 4 days at 23° C. and 210 rpm on a rotary shaker.

Culture broth obtained in the second pre-culture (second pre-cultivation broth) was inoculated at 5% (v/v) into a 60 L volumetric fermenter containing 30 L of Medium B. A third process of pre-culturing (third pre-cultivation) was carried out for 2 days at an aeration rate of 30 L per minute and a culturing temperature of 23° C. while adjusting the agitation speed so as to maintain the dissolved oxygen concentration within the range of 3 to 5 ppm.

Culture broth obtained in the third pre-culture (third pre-cultivation broth) was inoculated at 5% (v/v) into a 600 L volumetric fermenter containing 300 L of Medium B. A fourth process of pre-culturing (fourth pre-cultivation) was carried out for 2 days at an aeration rate of 300 L per minute and a culturing temperature of 23° C. while adjusting the agitation speed so as to maintain the dissolved oxygen concentration within the range of 3 to 5 ppm.

Culture broth obtained in the fourth pre-culture (fourth pre-cultivation broth) was inoculated at 5% (v/v) into a 6,000 L volumetric fermenter containing 4,000 L of Medium B. Fermentation was carried out for 8 days at a culturing temperature of 26° C. and an aeration rate of 2,000 L per minute while adjusting the agitation speed so as to maintain the dissolved oxygen concentration at 5 ppm. 200 L each of 20% sucrose solution was added on days 4 and 5 of the fermentation. 300 L each of 20% sucrose solution was further added on days 6 and 7 of the fermentation. Cercosporamide production was confirmed by the HPLC under the conditions indicated below.

TABLE 2

| Medium B: Medium Composition | |
| --- | --- |
| Glucose | 40 g |
| Potato granules (Agrawest Foods Ltd.) | 20 g |
| Polypepton | 10 g |
| Potassium dihydrogenphosphate | 5 g |
| Magnesium sulfate heptahydrate | 2.5 g |
| Antifoaming agent CB-442 (NOF Corp.) | 100 mg |
| Tap water | 1000 ml |

The medium was sterilized at 121° C. for 20 minutes without adjusting pH.

HPLC analysis was carried out under the conditions indicated below.
Separation column: Cadenza CD-C18, 4.6φ×75 mm (Imtakt Corp.)
Mobile phase: acetonitrile: 0.02% trifluoroacetic acid (40:60); eluted while changing solvent composition for 8 minutes (90:10)
Flow rate: 1.0 ml/minute
Detection: Ultraviolet absorption at 225 nm
Retention time: 5.4 minutes Example 3

Purification of Cercosporamide from Fermented Broth of *Lachnum fuscescens* SANK 19096 (FERM BP-10338)

The desired substance in the form of cercosporamide was confirmed by the HPLC under the conditions described in Example 2.

4,800 L of a fermented broth of *Lachnum fuscescens* SANK 19096 obtained in Example 2 was filtered using Celite 545 (Celite Corp.) as a filtration aid. 2,500 L of tap water was added to 781 kg of the resulting mycelial cake including the Celite and the cake as uniformly suspended therein. The material was then extracted by addition of 2,500 L of acetone to the suspension. 4,973 L of the resulting filtered extract was applied to a 80 L Diaion HP-20 column (Mitsubishi Chemical Corp.) equilibrated with about 500 L of a 50% aqueous acetone solution. The Diaion HP-20 column was washed with a 50% aqueous acetone solution. The liquid that passed solution through the column and washing solution were combined to obtain 5,500 L of solution.

75% (v/v) sulfuric acid was added to the resulting solution to adjust the pH to 3.0 followed by extraction by addition of 3,000 L of ethyl acetate. 4,218 L of solution extracted with ethyl acetate was washed with 1,000 L of 25% brine. The ethyl acetate was removed from 3,841 L of washed extract by concentration in vacuo. After concentrating to 81 L in vacuo, the ethyl acetate was further evaporated off using a 20 L volumetric rotary evaporator to obtain a concentrate.

About 10 L of the resulting concentrate was allowed to stand at 4° C. to crystalyze cercosporamide. 4,700 g of the resulting wet crystal was dried in vacuo to obtain 4,140 g of dry cercosporamide crystals.

Example 4

Production of Cercosporamide by *Lachnum fuscescens* SANK 19096 (FERM BP-10338)

A section of mycelia measuring about 5 mm on each side was cut out from a slant growing of strain SANK 19096 and suspended in about 2 ml of physiological saline. The suspension was then homogenized with a glass potter. The entire amount was aseptically inoculated into a 100 ml volumetric Erlenmeyer flask containing 20 ml of Medium B. Pre-culture was then carried out for 7 days at 23° C. and 210 rpm on a rotary shaker. The resulting pre-cultured broth was inoculated into a 500 ml volumetric Erlenmeyer flask containing 80 ml of Medium B having the same composition at 5% volume/volume (abbreviated as "v/v") inoculum size, and the fermentation was carried out for 10 days at 26° C. on a rotary shaker at 210 rpm. Extraction for the purpose of analysis was carried out in the manner described below. 0.4 ml of 3 M glycinate buffer (pH 3.2), 1 ml of acetone and 2 ml of n-butanol were added to 2 ml of fermented broth and cercosporamide was extracted by shaking for 10 minutes at room temperature. After centrifuging for 10 minutes at 3,000 rpm, 2 ml of saturated brine was added to the resulting solvent layer, and washing was carried out for 10 minutes at room temperature. An oily extract obtained by concentrating the solvent layer in vacuo was dissolved in 0.2 ml of a solution of dimethylsulfoxide and methanol (7:3). This extract solution was subjected to HPLC under the conditions described below. At this time, a peak having the same retention time as cercosporamide used as a control (retention time: 20.7 minutes) was observed.

| Medium Composition | |
| --- | --- |
| Glucose | 40 g |
| Potato granules (Agrawest Foods Ltd.) | 20 g |
| Polypepton | 10 g |
| Potassium dihydrogenphosphate | 5 g |

-continued

| Medium Composition | |
|---|---|
| Magnesium sulfate heptahydrate | 2.5 g |
| Antifoaming agent CB-442 (NOF Corp.) | 500 mg |
| Tap water | 1000 ml |

The medium was sterilized for 20 minutes at 121° C. without adjusting pH.

HPLC analysis was carried out under the conditions indicated below.
Column: Symmetry C-18, 4.6φ×150 mm (Waters Corp.)
Mobile phase: acetonitrile: 0.3% triethylamine phosphate buffer (pH 3.2) (5:95); eluted while changing solvent composition for 28 minutes (90:10)
Flow rate: 1.0 ml/minute
Detection: Ultraviolet absorption at 225 nm Example 5

Production of Cercosporamide by *Lachnum calycioides* SANK 12497 (FERM BP-10636)

A section of mycelia measuring about 5 mm on each side was cut from a slant growing of strain SANK 12497 followed by suspending in about 2 ml of physiological saline and homogenizing with a glass potter. The subsequent fermentation, extraction and analysis were carried out in the same manner as Example 4. By HPLC analysis, a peak coinciding with the retention time of cercosporamide was observed in the fermented broth (retention time: 20.7 minutes).

Example 6

Production of Cercosporamide by *Lachnum caesaliatum* SANK 10906 (FERM BP-10634)

A section of mycelia measuring about 5 mm on each side was cut from a slant growing of strain SANK 10906 followed by suspending in about 2 ml of physiological saline and homogenizing using a glass potter. The subsequent fermentation, extraction and analysis were carried out in the same manner as Example 4. By HPLC analysis, a peak coinciding with the retention time of cercosporamide was observed in the fermented broth (retention time: 20.7 minutes), thereby confirming that strain SANK 10906 produces cercosporamide.

Example 7

Production of Cercosporamide by *Pseudaegerita websteri* SANK 11006 (FERM BP-10635)

A section of mycelia measuring about 5 mm on each side was cut from a slant growing of strain SANK 11006 followed by aseptically inoculating into a 100 ml volumetric Erlenmeyer flask containing 20 ml of medium. The subsequent fermentation, extraction and analysis were carried out in the same manner as Example 4. By HPLC analysis, a peak coinciding with the retention time of cercosporamide was observed in the fermented broth (retention time: 20.7 minutes), thereby confirming that strain SANK 11006 produces cercosporamide.

INDUSTRIAL APPLICABILITY

Figure 1:
FIG. 1 shows a chromatogram obtained during HPLC analysis of cercosporamide obtained from a fermented broth of *Lachnum fuscescens* SANK 19096 (FERM BP-10338).

Cercosporamide can be produced according to the present invention, and cercosporamide produced according to said process can itself be used as an active ingredient of a pharmaceutical. In addition, this cercosporamide can also be used as a precursor of a cercosporamide derivative.

The invention claimed is:

1. A process for producing cercosporamide comprising:
   culturing a fungus belonging to the genus *Lachnum* and recovering cercosporamide from the culture thereof, wherein the fungus belonging to the genus *Lachnum* is at least one fungus selected from the group consisting of *Lachnum fuscescens* SANK 19096, *Lachnum calycioides* SANK 12497, and *Lachnum caesaliatum* SANK 10906.

2. A process for producing cercosporamide comprising culturing *Lachnum fuscescens* SANK 19096 and recovering cercosporamide from the culture thereof.

3. A process for producing cercosporamide comprising culturing *Lachnum calycioides* SANK 12497 and recovering cercosporamide from the culture thereof.

4. A process for producing cercosporamide comprising culturing *Lachnum caesaliatum* SANK 10906 and recovering cercosporamide from the culture thereof.

* * * * *